United States Patent [19]

Tench et al.

[11] 4,132,605
[45] Jan. 2, 1979

[54] METHOD FOR EVALUATING THE QUALITY OF ELECTROPLATING BATHS

[75] Inventors: Dennis M. Tench; Cameron A. Ogden, both of Thousand Oaks, Calif.

[73] Assignee: Rockwell International Corporation, El Segundo, Calif.

[21] Appl. No.: 754,476

[22] Filed: Dec. 27, 1976

[51] Int. Cl.² ............................................. G01N 27/46
[52] U.S. Cl. .................................. 204/1 T; 204/195 R
[58] Field of Search ................ 204/1 T, 195 H, 195 R

[56] References Cited

U.S. PATENT DOCUMENTS 3,925,168  12/1975  Costas .................................... 204/1 T

OTHER PUBLICATIONS

Adams, "Electrochemistry at Solid Electrodes", New York, Marcel Dekker, Inc., 1969, pp. 139, 143–160.

Willard et al., "Instrumental Methods of Analysis", 5th ed., 1974, pp. 652 & 653.

Primary Examiner—T. Tung
Attorney, Agent, or Firm—L. Lee Humphries; Craig O. Malin

[57] ABSTRACT

A working electrode is swept through a voltammetric cycle, including a metal plating range and a metal stripping range, for at least two baths of known plating quality and a bath whose quality is to be evaluated. The current utilized during the metal stripping range is correlated to the quality of the baths of known quality. The current utilized to strip the metal in the bath of unknown quality is compared to the correlation and its quality evaluated. In a preferred embodiment, an inert working electrode is swept by a function generator through the voltammetric cycle. A counter electrode immersed in the plating bath is coupled in series with the function generator and a coulometer to measure the charge during the metal stripping portion of the cycle.

9 Claims, 6 Drawing Figures

METHOD FOR EVALUATING THE QUALITY OF ELECTROPLATING BATHS

BACKGROUND OF THE INVENTION

1. Field of the Invention

This invention is related to the field of plating and particularly to the field of quality control of electroplating baths.

2. Description of the Prior Art

Electroplating is a complex process involving many ingredients n the plating bath. The concentration of some of these ingredients must be kept within close tolerances in order to obtain high quality deposits. In some caes, chemical analysis of individual constituents can be made regularly (such as pH measurement for acid content), and additions made as required. However, other constituents such as leveling agents (brighteners) and impurities cannot be individually analyzed on an economical or timely basis by a commercial plating shop. Their concentration is low and their quantitative analysis is complicated and subject to error.

A prior art method of controlling the ingredients in an electroplating bath is simply to make regular additions of the particular ingredients based upon rules of thumb established by experience. However, depletion of particular ingredients is not constant with time or with bath use. Consequently, the concentration of the ingredient in the bath eventually diminishes or builds up out of tolerance.

A further prior art method of plating bath control is to plate articles or samples and visually evaluate the plating quality to determine if the bath is performing satisfactorily. In standard Hull cell and "bone pattern" tests, a specially shaped test specimen is plated and then evaluated to determine the quality of the deposit along the shape. These are time-consuming tests which give only rough approximations of the concentration of constituents in the bath.

The electroplating of through-hole interconnection in the manufacture of multilayer printed circuit boards is an example where high quality plating is required. It is known that the concentration of leveling agent, or brightener, must be maintained in the low ppm range in order to obtain acceptable deposits on printed circuit boards. The concentration of brightener fluctuates because of oxidation at the anode, reduction and inclusion at the cathode, and chemical degradation. When the brightener level is insufficient, deposits are burnt and powdery; whereas, excess brightener induces brittleness and non-uniform deposition ("fisheyes"). Hull cell tests, "bone pattern" tests, and tensile tests, combined with the periodic additions of fresh brightener, were, until the present invention, the only methods available to maintain a controlled brightener concentration. Since these methods are unreliable, circuit board quality suffers and rejection rates are high.

SUMMARY OF THE INVENTION

It is an object of the invention to provide a method and device for evaluating the quality of electroplating baths.

It is a further object of the invention to provide a method and device for determining the effective concentration of additives in electroplating baths.

It is a further object of the invention to provide a method and device for determining the effective concentration of leveling agents in electroplating baths.

It is a further object of the invention to provide a method and device for determining the effective concentration of leveling agents in copper electroplating baths used for plating printed circuit boards.

According to the invention, a working electrode is swept through a voltammetric cycle, including a metal plating range and a metal stripping range, for at least two baths of known plating quality and a bath whose quality is to be evaluated. The integrated or peak current utilized during the metal stripping range is correlated with the quality of the baths of known quality. The integrated or peak current utilized to strip the metal in the bath of unknown quality is compared to the correlation and its quality evaluated. In a preferred embodiment, an inert working electrode is swept by a function generator through the voltammetric cycle. A counter electrode immersed in the plating bath is coupled in series with the function generator and a coulometer to measure the charge during the stripping portion of the cycle.

These and other objects and features of the present invention will be apparent from the following detailed description, taken with reference to the accompanying drawings.

DESCRIPTION OF THE PREFERRED EMBODIMENT

In performing their function, many additives to electroplating baths appreciably affect the rate of electrodeposition of the metal at a given electrode potential. The present invention makes use of this effect to determine the concentration of a particular additive in the solution. A small amount of metal is electrodeposited onto an inert electrode (e.g., Pt, Au, etc.) under controlled conditions of electrode potential and mass-transport in the solution. The amount of metal deposited is determined by integrating the current peak arising from re-dissolution or "stripping" of the deposited metal from the surface as the electrode potential is swept anodic at a known rate. The quantity of metal deposited, and subsequently re-dissolved, is related to the concentration of additives affecting the rate of deposition. The cathodic current required to deposit the metal is also an indication of the deposition rate, but it is intrinsically less precise because of other reduction reactions (such as the reduction of hydrogen or organic compounds in the bath) occurring during the cathodic portion of the voltammetric cycle.

The present invention has proven particularly valuable for determining the concentration of leveling agents and brighteners in the bath because these additives induce leveling of the deposit by inhibiting deposition at peaks, where its concentration remains high, and enhancing deposition in recesses, where its concentration becomes depleted as it is included in the deposit. Of course, the invention is applicable to determining the effect of any variable or ingredient whose intensity or concentration either decreases or increases the deposition rate of the bath.

The method of the present invention differs from conventional voltammetric analysis in which the substance to be determined is, itself, absorbed and then stripped from the electrode surface. This requires that the electrolyte be free of other ingredients which are absorbed with the substance being analyzed. This is not a suitable method for determining the quantity of low concentration additives in a plating bath because the quantity of the additive cannot be separated from the large quantity of metal being deposited.

Figure 1:
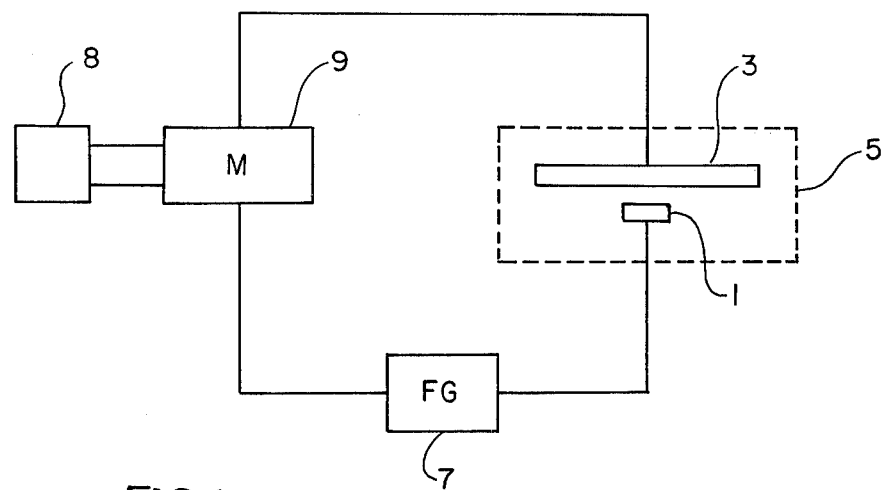
FIG. 1 is a schematic wiring diagram of a device according to an embodiment of the invention.

FIG. 1 is a schematic wiring diagram showing a device for practicing the method of the present invention. A working electrode 1 and a counter electrode 3 are immersed in a bath in cell 5. The counter electrode is selected and designed so as not to be easily polarized in the particular bath being evaluated. This is accomplished, in part, by making the counter electrode large relative to the working electrode and by placing it close to the working electrode.

A function generator 7 sweeps the working electrode 1 through a voltage vs. time cycle at a specific rate while a coulometer 9 measures the coulombs (amp-seconds) flowing between the counter electrode 3 and the working electrode 1 during the metal stripping portion of the voltammetric cycle. The coulometer may be an ammeter whose output can be fed into an x-y recorder for determining the coulombs utilized during the stripping portion of the cycle, or the output can go directly into a microprocessor or minicomputer 8 for direct correlation and comparison of the coulombs utilized.

Figure 2:
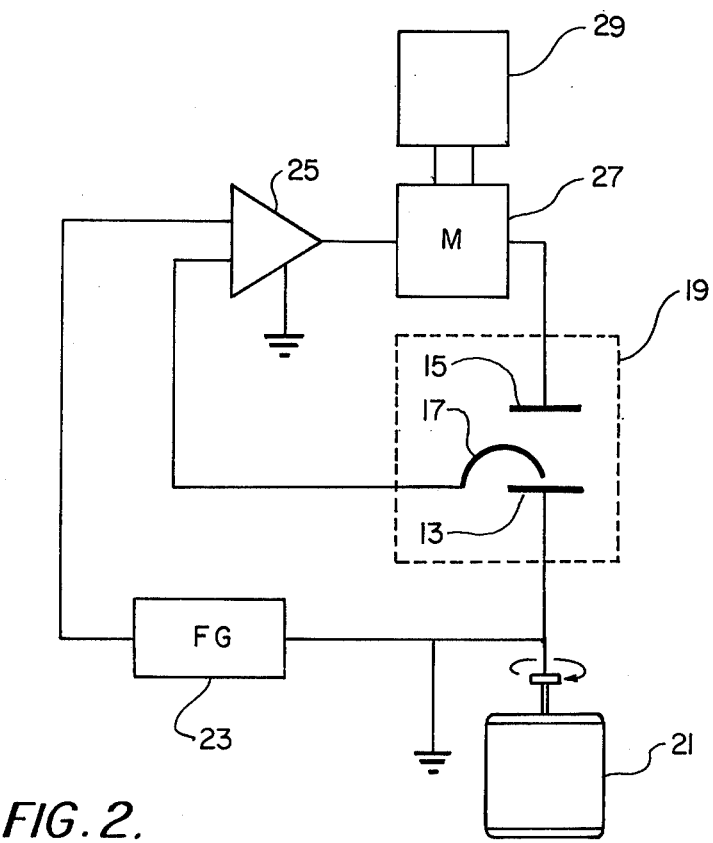
FIG. 2 is a schematic wiring diagram of a device according to a second embodiment of the invention.

FIG. 2 shows the schematic wiring diagram for a more elaborate device for practicing the present invention. Three electrodes, a working electrode 13, a counter electrode 15, and a reference electrode 17, are immersed in a bath in cell 19. To establish relative motion between the working electrode 13 and the bath, a motor 21 is used to rotate the working electrode 13 to which contact is made by slip brushes.

In one embodiment, the working electrode 13 is platinum and the counter electrode 15 is platinum — 10% rhodium, although any conductive material, such as gold, which is inert in the particular bath, can be used. The rotatable working electrode 13 has a flat, polished surface, 0.13 cm² in area, mounted flush with the end of a 1.27 cm diameter Kel-F cylinder. The reference electrode 17 is, conveniently, a saturated calomel reference electrode (SCE).

A function generator 23 and an electronic potentiostat 25 are used to control the potential relative to the reference electrode 17. A digital coulometer 27 measures the coulombs flowing during the stripping portion of the voltammetric cycle. For laboratory testing of the method, the function generator 23 was a Princeton Applied Research Corporation (PAR) Model 175 universal programmer, the potentiostat 25 was a PAR Model 173 potentiostat/galvanostat, and the coulometer 27 was a PAR 179 digital coulometer or an x-y recorder for obtaining a cyclic voltammogram (amps vs. volts).

A microprocessor or minicomputer 29 can be coupled to the digital coulometer to compare the measured coulombs with a previously established correlation. The microprocessor or minocomputer 8, 29, shown in FIGS. 1 and 2, can be coupled to the circuit so that they are triggered either manually or by a suitable signal from the function generator 7, 23, or from the working electrode 1, 13.

Figure 3:
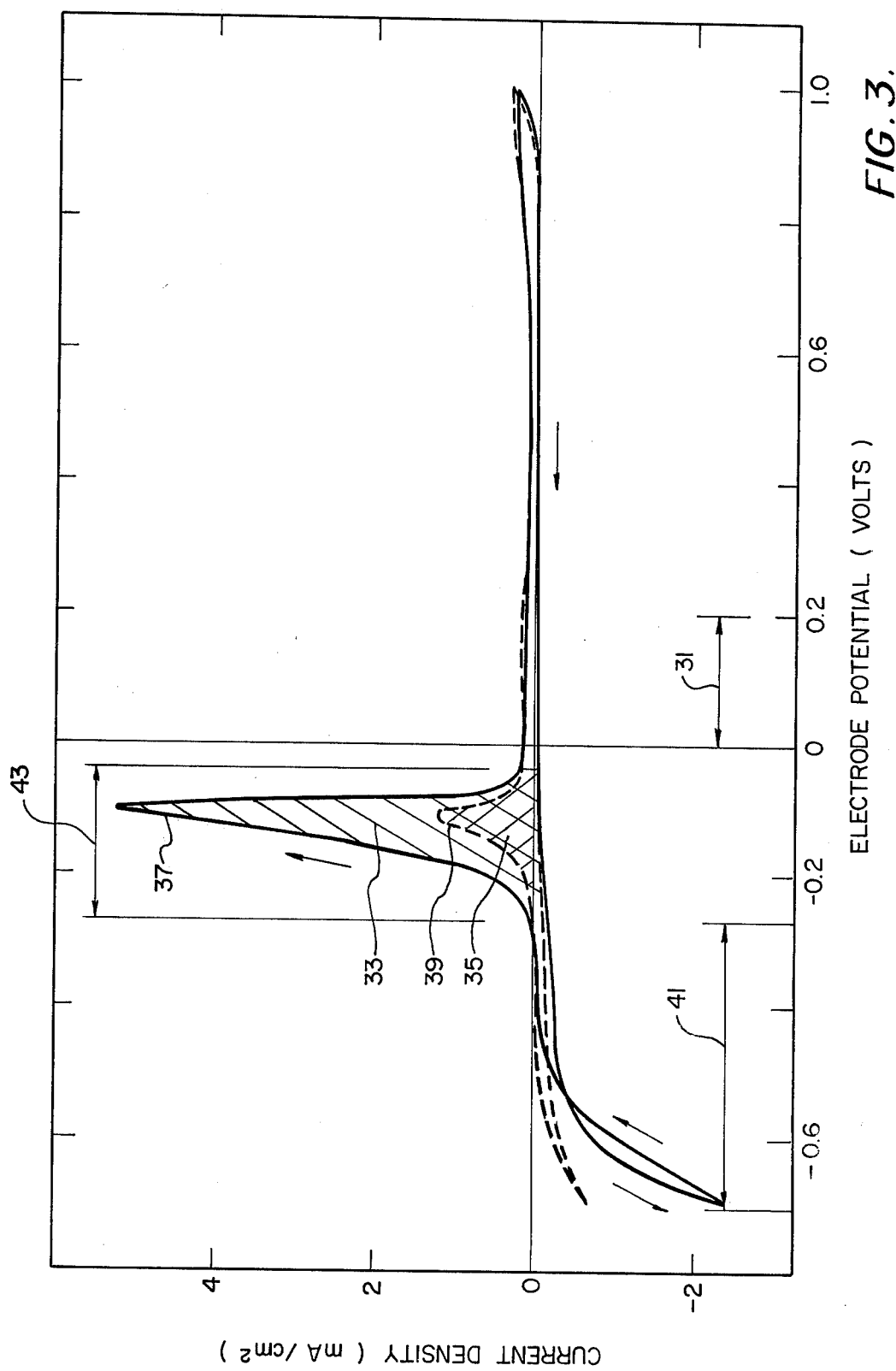
FIG. 3 shows two cyclic voltammographs illustrating the method of using the device of FIG. 2.

FIG. 3 shows two cyclic voltammographs obtained utilizing an x-y recorder in the device of FIG. 2. The potential of the working electrode 13 was driven by the function generator 23 at a linear rate of 0.050 volt/sec so that the abcissa of the voltammograph can be read as either volts or seconds, with one scale unit 31 being equal to either 0.2 volt or 4 seconds. Thus, the areas 33, 35 under the curves 37, 39 are equal to amp-sec, or coulombs. Curve 37 was obtained for one condition of the bath and curve 39 for another condition of the bath, as discussed below. The arrows show the direction in which the voltage is sweeping. Although the positions of the peaks shown in FIG. 3 are shifted for baths of different composition, the general shape of the voltammograph is the same for baths for plating any of the usual metals such as copper, nickel, chromium, zinc, tin, gold, silver, lead, and cadmium.

The particular voltammographs of FIG. 3 were obtained utilizing a copper pyrophosphate plating bath having the following composition:

Copper, $Cu^{+2}$: 22–38 g/l
Pyrophosphate, $(P_2O_7)^{-4}$: 150–250 g/l
Orthophosphate $(HPO_4)^{-2}$: < 110 g/l
Ammonia, $NH_3$: 1–3 g/l
Nitrate, $NO_3^-$: 5–10 g/l
Organic Additive: as required
pH: 8.0–8.8
Temperature: 50°–60° C.

The organic additive used is a proprietary leveling agent or brightener PY61-H obtained from the M&T Chemical Corporation, whose active ingredient is a dimercaptothiadiazole.

In the bath utilized for curve 37, the concentration of organic additive was 1.0 ml/l, whereas in the bath for curve 39 the concentration was 2.0 ml/l. The portion of the voltammographs under line 41 is the metal plating (cathodic) portion and the portion under line 43 is the metal stripping (anodic) portion of the voltammetric cycle. The portion to the right of line 43 is a continuation of the oxidation portion of the cycle after all metal has been stripped from the inert electrode. There is some slight current flow in this portion caused by oxidation of the electrode and oxidation of organic compounds in the bath. Although copper stripping is completed by − 0.050 volt, the sweep is extended to 1.0 volt, since this extended sweep gives more reproducible results and achieves a steady state condition after only about five sweep cycles.

At sweep rates faster than 0.05 volt/sec, the stripping peaks are broader and less reproducible, whereas slower sweeps are unnecessarily time-consuming. Sweeps to a more cathodic limit than − 0.7 volt result in broader stripping peaks.

To achieve maximum sensitivity, there must be sufficient relative motion between the working electrode and the bath to maintain a uniform supply of plating ingredients at the electrode surface. Without such motion, the bath becomes depleted at the surface and the deposition rate obtained does not reflect to correct rate for the bulk solution. In the embodiment shown in FIG. 2, the working electrode 13 is rotated by motor 21 to obtain controlled relative motion between it and the plating bath. Other means of obtaining relative motion can be used, such as a pump for moving the bath across the face of the electrode.

According to the method of the present invention, voltammetric cycles (FIG. 3) are first run under controlled conditions of electrode potential and mass-transport in the solution for baths of known quality, or of known concentration of additives, to obtain the current or coulombs during the stripping range 43 of the cycle. The quality or concentration is then correlated with the peak stripping current or with the stripping coulombs to obtain the concentration as a function of the peak stripping current or of the stripping coulombs.

In some cases, significant variations in the stripping current are observed from day to day for a particular bath composition and are probably caused by uncontrolled variables, such as changes in the working electrode surface. Such variations can be mitigated by measuring the stripping current utilized by a fixed standard immediately before or after making the desired measurement and then utilizing the ratio of the two measurements to obtain the correlation between stripping current and concentration of ingredients.

In a further embodiment of the invention, variations in stripping current caused by uncontrolled variables are mitigated by using an internal standard provided by a static working electrode in the same bath. As previously mentioned, when there is no relative motion between the bath and the surface of the working electrode, the concentration of the additives at the surface decreases with continued potential cycling until a steady state level is established. The level established is determined by the rate of diffusion of the additive in the bath. For the dimercaptothiadiazole brightener used in the previously-mentioned copper pyrophosphate bath, the stripping current obtained with a static working electrode corresponds to a bath of close to zero brightener concentration.

Figure 4:
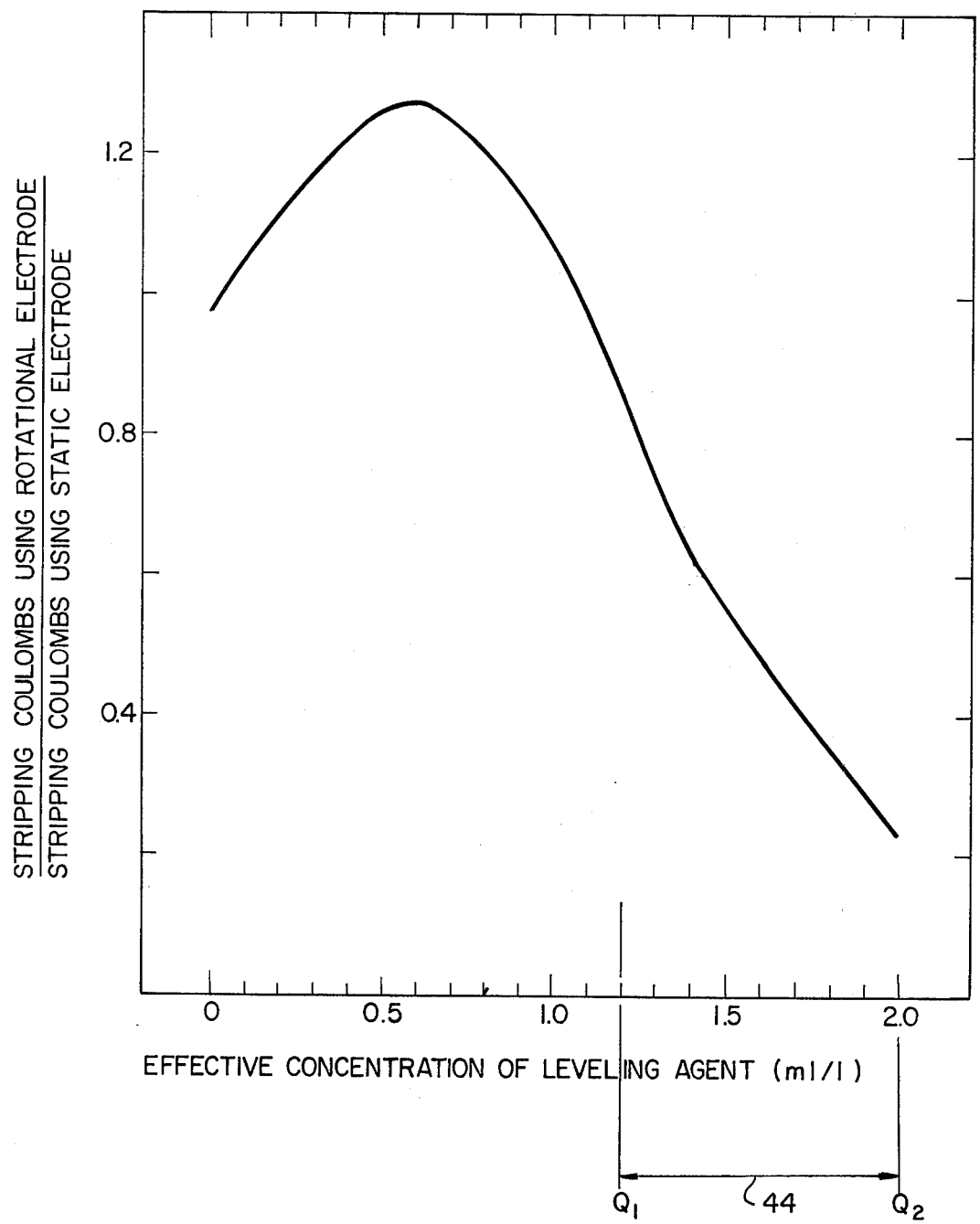
FIG. 4 is a curve showing the correlation between coulombs utilized during the stripping range (unitized to an internal standard) and the concentration of a leveling agent.

FIG. 4 shows a correlation of the stripping coulombs as a function of the effective concentration of leveling agent for a copper pyrophosphate bath. The correlation need not be for an absolute quantity of leveling agent. For example, the correlation can be for a particular quality level, as shown by $Q_1$ and $Q_2$. The distance 44 shown between $Q_1$ and $Q_2$ represents a bath of acceptable quality for a particular type defect (foldbacks, as discussed later), between two quality extremes, $Q_1$ and $Q_2$. To mitigate uncontrolled variables, a stationary electrode (as compared to a 2500 rpm rotational electrode) has been used as an internal standard to obtain the ratio shown on the ordinate. As previously mentioned, separate external standards could also be used to obtain the ratio. In some cases, sufficient accuracy could be obtained by plotting stripping coulombs directly, or by plotting peak stripping current. In any case, the general shape of the curve would resemble the curve shown in FIG. 4.

The correlation shown in FIG. 4 is used to determine the quality or concentration of a leveling agent in an unknown bath. A similar ratio of stripping coulombs is determined for the unknown bath and then compared to the correlation in FIG. 4 to obtain the corresponding quality or concentration. Since this method is based upon comparison, the standards used to obtain the correlation should be representative of the condition of the unknown bath, or any variations between the baths should be accounted for. Similarly, the unknown bath should be operated under similar conditions of electrode potential and mass-transport (temperature, atmosphere, agitation, etc.) as for the standards, or any variations in operation should be accounted for.

For coulomb ratios greater than about 1.0 for the unknown bath, two values of concentration are obtained because of the peak in the curve of FIG. 4. However, the correct concentration can readily be chosen, because the voltammetry peak is shifted cathodically by as much as 0.2 volt for concentrations less than 0.5 ml/l. Additionally, for most practical purposes, any concentration of leveling agent less than shown by $Q_1$ (1.2 ml/l) indicates insufficient concentration for the minimum quality level, thus indicating that additional leveling agent is required.

Figure 5:
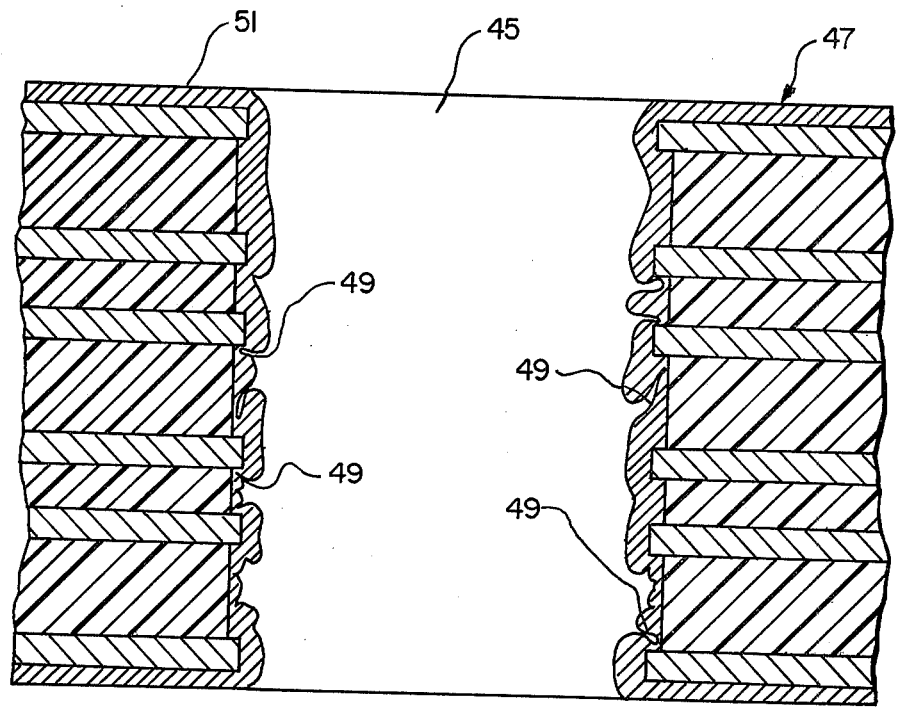
FIG. 5 is a schematic representation of a partial cross-section of a through-hole in a printed circuit board which was plated with a bath having an insufficient quantity of leveling agent.
Figure 6:
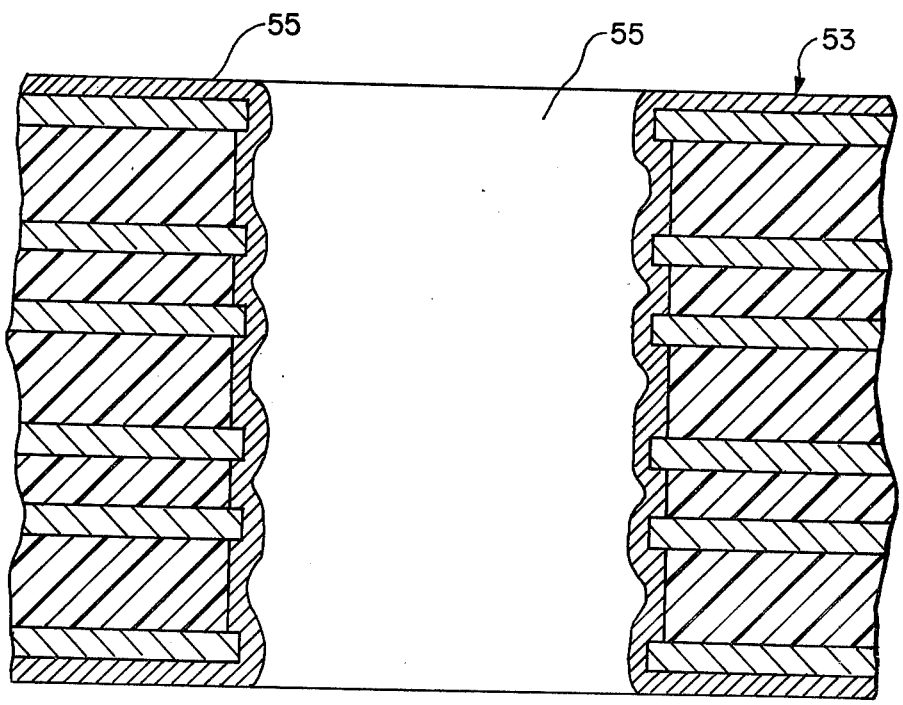
FIG. 6 is a schematic representation of a cross-section similar to FIG. 5 except for a circuit board plated with a sufficient quantity of leveling agent.

In work leading to the present invention, it was discovered that the concentration of leveling agent had a strong influence on the amount of foldback defects obtained during copper plating of through-holes in circuit boards. FIG. 5 shows a through-hole 45 in a circuit board 47 containing numerous foldback defects 49 in the copper deposit 51 when an effective concentration of less than 1.2 ml/l of leveling agent (PY61-H) was used in the bath. However, when a similar circuit board 53 was copper-plated with a concentration of leveling agent from 1.2-2.0 ml/l, the foldback defects did not occur, as shown in FIG. 6 for copper plate 55. Thus, foldback defects and other plating problems related to the plating rate can readily be overcome by controlling the concentration of additives in the plating bath utilizing the method and device of the present invention.

Although there is a wide variety of plating baths for various plating metals, including copper, nickel, chromium, zinc, tin, lead, gold, silver, and cadmium, the same scientific principles are involved in their application. Leveling agents such as the dimercaptothiadiazole used in copper phosphate plating baths and peptone used in tin or tin-lead fluoborate plating baths affect the metal deposition rate. Thus, it is clear that the present invention is applicable for evaluating the quality or concentration of leveling agents and other additives which affect the plating rate in all such plating baths and for all additives or variables which have an effect on plating rates.

Numerous variations and modifications may be made without departing from the present invention. Accordingly, it should be clearly understood that the form of the present invention described above and shown in the accompanying drawings is illustrative only and is not intended to limit the scope of the present invention.

What is claimed is:

1. A method of determining the effective quantity of organic leveling agent in a bath for electroplating a metal, comprising the steps of:
   obtaining a plurality of plating baths, each bath having a different effective quantity of organic leveling agent;
   sweeping for each of said baths an inert, working electrode at a predetermined rate through a plurality of voltammetric cycles until a condition of steady state is obtained, each of said voltammetric cycles including a metal plating range and a metal stripping range for each of said baths of said plurality of baths, each of said voltammetric cycles comprising a sweeping of a voltage toward one polarity followed by a sweeping of said voltage toward a reverse of said one polarity to complete said cycle;

measuring the coulombs utilized during said metal strpping range of said cycle for each of said baths of said plurality of baths, whereby a correlation is obtained between the effective quantity of organic leveling agent and said coulombs utilized during said metal stripping range;

obtaining a bath having an unknown quantity of organic leveling agent;

sweeping for said unknown bath an inert, working electrode at said predetermined rate through a plurality of voltammetric cycles until a condition of steady state is obtained, each of said voltammetric cycles including a metal plating range and a metal stripping range for said bath having an unknown quantity of organic leveling agent, each of said voltammetric cycles comprising a sweeping of a voltage toward one polarity followed by a sweeping of said voltage toward a reverse of said one polarity to complete said cycle;

measuring the coulombs utilized during said metal stripping range of said cycle for said bath having an unknown quantity of leveling agent; and choosing from said correlation a quantity of organic leveling agent which corresponds to said coulombs utilized for said bath having an unknown quantity of organic leveling agent.

2. A method of determining if a bath for electroplating a metal has an acceptable, effective quantity of organic leveling agent, comprising the steps of:

a. sweeping a working electrode through at least one voltammetric cycle comprising a sweeping of voltage toward one polarity followed by a sweeping of voltage toward a reverse of said one polarity to complete a cycle, said voltammetric cycle including a metal plating range and a metal stripping range, for a bath having a minimum acceptable effective quantity of organic leveling agent;

b. measuring the coulombs utilized during said metal stripping range of said cycle for said bath having a minimum acceptable effective quantity of organic leveling agent;

c. repeating steps (a) and (b) for a bath having a maximum acceptable effective quantity of organic leveling agent;

d. repeating steps (a) and (b) for a bath having an unknown quantity of organic leveling agent, whereby said bath of unknown quantity of organic leveling agent has an acceptable, effective quantity of organic leveling agent when the coulombs utilized during step (d) are equal to or greater than the coulombs utilized during step (b) but no greater than the coulombs utilized during step (c).

3. The method as claimed in claim 2, wherein said step of sweeping a working electrode comprises sweeping a working electrode both while there is no relative motion and while there is relative motion between said bath and said working electrode; and wherein said step of measuring the coulombs includes obtaining the ratio of coulombs utilized with relative motion divided by the coulombs utilized with no relative motion.

4. The method as claimed in claim 2, wherein said bath for electroplating a metal comprises a bath for electroplating copper.

5. The method as claimed in claim 2, wherein:
said step of sweeping a working electrode comprises sweeping a working electrode while there is relative motion between said baths and said working electrode.

6. The method as claimed in claim 5, wherein said relative motion is obtained by utilizing a rotating working electrode.

7. The method as claimed in claim 2, wherein said step of sweeping comprises sweeping said working electrode through a plurality of said cycles until a condition of steady state is obtained.

8. The method as claimed in claim 2, wherein said voltammetric cycle extends past said metal stripping range.

9. A method of determining the effective amount of organic leveling agent in a metal plating bath comprising:

a. submerging a working electrode in a quantity of the bath to be tested;

b. placing a reference electrode adjacent to said working electrode;

c. sweeping said working electrode at a predetermined rate through a plurality of voltammetric cycles until a condition of steady state is obtained, each of said voltammetric cycles comprising a sweeping of voltage toward one polarity followed by a sweeping of said voltage toward a reverse of said one polarity to complete said cycle, said voltammetric cycle including a metal plating range and a metal stripping range;

d. measuring the coulombs utilized during said metal stripping range of said cycle;

e. thereafter repeating steps (c) and (d) with baths having varying known leveling agent content; and f. finally determining the amount of effective leveling agent in an unknown bath by:

i. sweeping said working electrode at a predetermined rate through a plurality of voltammetric cycles until a condition of steady state is obtained, each of said voltammetric cycles comprising a sweeping of voltage toward one polarity followed by a sweeping of said voltage toward a reverse of said one polarity to complete said cycle, said voltammetric cycle including a metal plating range and a metal stripping range;

ii. measuring the coulombs utilized during said metal stripping range of said cycle; and iii. comparing the measured coulombs with said prior measurements of (d) above.

* * * * *

REEXAMINATION CERTIFICATE (515th)
United States Patent [19]
Tench et al.

[11] B1 4,132,605
[45] Certificate Issued  Jun. 10, 1986

[54] METHOD FOR EVALUATING THE QUALITY OF ELECTROPLATING BATHS

[75] Inventors: Dennis M. Tench; Cameron A. Ogden, both of Thousand Oaks, Calif.

[73] Assignee: Rockwell International Corporation, El Segundo, Calif.

Reexamination Request:
No. 90/000,670, Nov. 23, 1984

Reexamination Certificate for:
Patent No.: 4,132,605
Issued: Jan. 2, 1979
Appl. No.: 754,476
Filed: Dec. 27, 1976

[51] Int. Cl.$^4$ .............................................. G01N 27/46
[52] U.S. Cl. ..................................... 204/1 T; 204/434
[58] Field of Search ................. 204/1 T, 400, 413, 434

[56] References Cited
U.S. PATENT DOCUMENTS 3,215,609  11/1965  Chapdelaine ...................... 204/434
3,859,193  1/1975  Bednarski et al. ................. 204/413
4,146,437  3/1979  O'Keefe .

OTHER PUBLICATIONS

Kolthoff et al., Polarography, 2nd. ed., (1952), vol. 1, pp. 399-413.
D. M. MacArthur, "A Study of Gold Reduction and Oxidation in Aqueous Solutions", J. Electrochemical Soc.: Electrochemical Science and Technology, Jun. 1972, pp. 672-677.

*Primary Examiner*—T. Tung

[57] ABSTRACT

A working electrode is swept through a voltammetric cycle, including a metal plating range and a metal stripping range, for at least two baths of known plating quality and a bath whose quality is to be evaluated. The current utilized during the metal stripping range is correlated to the quality of the baths of known quality. The current utilized to strip the metal in the bath of unknown quality is compared to the correlation and its quality evaluated. In a preferred embodiment, an inert working electrode is swept by a function generator through the voltammetric cycle. A counter electrode immersed in the plating bath is coupled in series with the function generator and a coulometer to measure the charge during the metal stripping portion of the cycle.

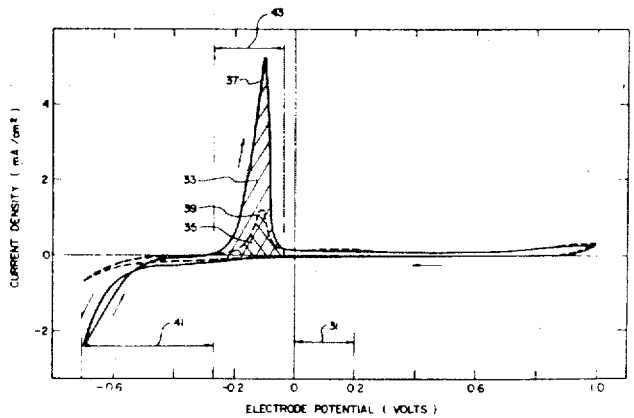

REEXAMINATION CERTIFICATE
ISSUED UNDER 35 U.S.C. 307

THE PATENT IS HEREBY AMENDED AS
INDICATED BELOW.

Matter enclosed in heavy brackets [] appeared in the patent, but has been deleted and is no longer a part of the patent matter, printed in italics indicates additions made to the patent.

AS A RESULT OF REEXAMINATION, IT HAS BEEN DETERMINED THAT:

Claims 1-9 are cancelled.

New claims 10 and 11 are added and determined to be patentable.

*10. A method of determining the effective quantity of organic leveling agent in a bath for electroplating a metal, comprising the steps of:*
  *a. obtaining a plurality of plating baths, each bath having a different effective quantity of organic leveling agent;*
  *b. sweeping for each of said baths an inert, working electrode at a predetermined rate through a plurality of voltammetric cycles until a condition of steady state is obtained, each of said voltammetric cycles including a metal plating range, and a metal stripping range for stripping all of the metal deposited during said metal plating range, each of said voltammetric cyles comprising a sweeping of a voltage toward one polarity followed by a sweeping of said voltage toward a reverse of said one polarity to complete said cycle, said sweeping being done while there is no relative motion between said bath and said electrode;*
  *c. repeating step (b) above except doing said sweeping while there is relative motion between said bath and said electrode;*
  *d. measuring the coulombs utilized during said metal stripping range of said cycle for each of said baths for both steps (b) and (c);*
  *e. obtaining a ratio between said coulombs utilized with relative motion and coulombs utilized with no relative motion, whereby a correlation is obtained between the effective quantity of organic leveling agent and said ratio of coulombs utilized during said metal stripping range;*
  *f. obtaining a bath having an unknown quantity of organic leveling agent;*
  *g. repeating step (b) above for said unknown bath while there is no relative motion between said bath and said electrode;*
  *h. repeating step (b) above for said unknown bath except doing said sweeping while there is relative motion between said bath and said electrode;*
  *i. measuring the coulombs utilized during said metal stripping range of said cycle for said unknown bath for both steps (g) and (h);*
  *j. obtaining a ratio between said coulombs utilized with relative motion and coulombs utilized with no relative motion for said unknown bath; and*
  *k. choosing from said correlation a quantity of organic leveling agent which corresponds to said ratio for said unknown bath.*

*11. A method of determining if a bath for electroplating a metal has an acceptable, effective quantity of organic leveling agent, comprising the steps of:*
  *a. sweeping a working electrode through at least one voltammetric cycle comprising a sweeping of voltage toward one polarity followed by a sweeping of voltage toward a reverse of said one polarity to complete a cycle, said voltammetric cycle including a metal plating range and a metal stripping range, for a bath having a minimum acceptable effective quantity of organic leveling agent, said sweeping being done both while there is no relative motion and while there is relative motion between said bath and said working electrode;*
  *b. measuring the coulombs utilized during said metal stripping range of said cycle for said bath having a minimum acceptable effective quantity of organic leveling agent, and obtaining the ratio of coulombs utilized with relative motion divided by the coulombs utilized with no relative motion;*
  *c. repeating steps (a) and (b) for a bath having a maximum acceptable effective quantity of organic leveling agent;*
  *d. repeating steps (a) and (b) for a bath having a unknown quantity of organic leveling agent, whereby said bath of unknown quantity of organic leveling agent has an acceptable, effective quantity of organic leveling agent when the ratio obtained during step (d) is within the range established by steps (b) and (c).*

* * * * *